United States Patent
Mutlu et al.

(10) Patent No.: US 9,224,309 B2
(45) Date of Patent: Dec. 29, 2015

(54) TEACHING SYSTEM FOR IMPROVING INFORMATION RETENTION BASED ON BRAIN-STATE MONITORING

(75) Inventors: Bilge Mutlu, Fitchburg, WI (US); Daniel J. Szafir, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 757 days.

(21) Appl. No.: 13/437,699

(22) Filed: Apr. 2, 2012

(65) Prior Publication Data
US 2013/0260361 A1 Oct. 3, 2013

(51) Int. Cl.
*A61B 5/048* (2006.01)
*A61B 5/0482* (2006.01)
*G09B 19/00* (2006.01)

(52) U.S. Cl.
CPC ............... *G09B 19/00* (2013.01); *A61B 5/048* (2013.01); *A61B 5/0482* (2013.01)

(58) Field of Classification Search
CPC ....... G09B 19/00; A61B 5/048; A61B 5/0482
USPC ........................................................ 434/365
See application file for complete search history.

(56) References Cited

U.S. PATENT DOCUMENTS

| | | | | |
|---|---|---|---|---|
| 6,097,981 | A * | 8/2000 | Freer ............................ | 600/545 |
| 6,402,520 | B1 * | 6/2002 | Freer ............................ | 434/236 |
| 2004/0072133 | A1 * | 4/2004 | Kullok et al. ................. | 434/236 |
| 2004/0230549 | A1 * | 11/2004 | Freer et al. ...................... | 706/61 |
| 2008/0220400 | A1 * | 9/2008 | Cox et al. ...................... | 434/236 |
| 2008/0275358 | A1 * | 11/2008 | Freer et al. .................... | 600/544 |
| 2009/0124921 | A1 * | 5/2009 | Milgramm et al. ........... | 600/544 |

OTHER PUBLICATIONS

Slides from a faculty/student presentation at the University of Wisconsin—Madison, delivered Dec. 1, 2010.

* cited by examiner

*Primary Examiner* — Sam Yao
*Assistant Examiner* — Thomas Hong
(74) *Attorney, Agent, or Firm* — Boyle Fredrickson, S.C.

(57) ABSTRACT

A computer-based education system monitors brain activity of the student to produce an "engagement" signal that may be compared against a dynamic threshold to identify a plurality of points demarcating periods of declining attention. These points are used to trigger modifications to the presentation of the educational program to promote student retention of the present information.

18 Claims, 4 Drawing Sheets

TEACHING SYSTEM FOR IMPROVING INFORMATION RETENTION BASED ON BRAIN-STATE MONITORING

BACKGROUND OF THE INVENTION

The present invention relates to computer-based education (CBE) systems and, in particular, to a computer-based education system that responds to a measured brain state to improve the retention of presented information.

BACKGROUND OF THE INVENTION

Computer-based education (CBE) holds significant promise for instructing individuals using educational programs implemented via computers instead of human instructors. In its simplest form, such CBE may present educational material in a traditional linear format of a human lecturer (for example, pre-recorded lectures to be played by the software) or such software may adopt a more complex organizational structure of interlinked audio and visual materials navigated by the student under computer supervision. Often computer-based educational programs provide a framework that includes practice exercises and tests and will modify the educational program based on the results of those exercises and tests.

Computer-based education can greatly expand access to high-quality educational materials prepared by talented educators and can leverage the efforts of skilled educators beyond the scope normally possible with an individual lecturer/student model. Nevertheless computer-based education is not yet as effective as the best human tutors.

SUMMARY OF THE INVENTION

The present invention significantly increases the effectiveness of computer-based education by adjusting the presentation of CBE material according to a monitored brain state of the student. In one embodiment, EEG sensing is used to identify changes in engagement or attention by the student and to trigger attention-promoting interventions based on a dynamic engagement threshold. More specifically, in one embodiment the present invention provides a computer-based education system having a brain activity monitor providing a monitoring of brain activity of the student. An electronic computer communicating with the brain activity monitor presents an educational program to the student while it receives a signal from the brain activity monitor indicating a brain activity of the student to provide an engagement signal indicating student attention. The engagement signal is compared to a dynamic threshold to identify a plurality of points demarcating periods of declining attention and the presentation of the educational program is modified to promote student attention at times of the identified points.

It is thus a feature of at least one embodiment of the invention to practically identify points of declining engagement applicable to a wide range of students and educational materials. The creation of a dynamic threshold accommodates differences in individuals to successfully initiate attention-enhancing stimulation for those individuals.

The brain activity monitor may be, for example, an EEG monitor or a functional near infrared imaging monitor.

It is thus a feature of at least one embodiment of the invention to provide a system that can use with currently developed low-cost brain monitoring equipment suitable for use and ownership by individual students.

The brain activity monitor may be an EEG monitor providing a signal including, alpha, beta and theta waves from the brain.

It is thus a feature of at least one embodiment of the invention to provide a system that exploits the information in well-understood and detected categories of brain waves.

The engagement signal may comprise a functional combination of multiple brain waves increasing with increasing beta wave strength and decreasing with increasing alpha and theta wave strength.

It is thus a feature of at least one embodiment of the invention to provide a simple mathematically tractable formula for extracting student engagement from brainwave activity.

The dynamic threshold may be based on historical measures of the student's brain waves.

It is thus a feature of at least one embodiment of the invention to use the student's characteristic brain waves to "calibrate" the engagement signal and thus to provide a system that may better accommodate a range of different students.

Alternatively or in addition, the dynamic threshold may be based on a slope of decrease in the engagement signal.

It is thus a feature of at least one embodiment of the invention to provide a system for determining engagement with reduced sensitivity to absolute brainwave values such as may fluctuate for different educational materials and among students.

Alternatively or in addition the dynamic threshold may be based on a comparison of a slope in decrease in the engagement signal for two different time windows applied to the engagement signal.

It is thus a feature of at least one embodiment of the invention to provide a dynamic threshold that can de-emphasize minor short-term fluctuations in attention.

The educational program may be presented by a representation of a human speaker (for example an avatar or electromechanical robot) and the modification of the presentation may modify a gesture of the representation of the human speaker using hand movements.

It is thus a feature of at least one embodiment of the invention to tap into techniques naturally used by educators to bolster attention.

The hand movements may be selected from the categories of iconic, metaphoric, deictic, and beat gestures.

It is thus a feature of at least one embodiment of the invention to permit nuanced use of gesture such as provides an additional channel of communication.

The educational program may include an audio signal providing spoken text and the modification of the presentation modifies the audio signal. The audio signal may be modified by techniques including modification selected from the group consisting of changing a volume of the audio signal and augmenting the audio signal with nontext audio signals. When the educational program includes a video display, the modification of the presentation may provide camera effects to the video display selected from the group consisting of: change in camera angle, palming, shaking, zooming, and changing illumination.

It is thus a feature of at least one embodiment of the invention to provide a mechanism for promoting attention in environments where hand gestures may not be readily modified, for example, in a pre-recorded lecture by a human educator.

Alternatively or in addition the modification of the presentation may interrupt the presentation to require student input.

It is thus a feature of at least one embodiment of the invention to promote student attention by engaging the student for input.

The student input may provide a set of evaluation questions answered by the student.

It is thus a feature of at least one embodiment of the invention to employ a form of student input that may exercise recall of the information and that may provide for useful feedback for the computer based instruction system.

These particular objects and advantages may apply to only some embodiments falling within the claims and thus do not define the scope of the invention.

DETAILED DESCRIPTION OF THE PREFERRED EMBODIMENT

Figure 1:
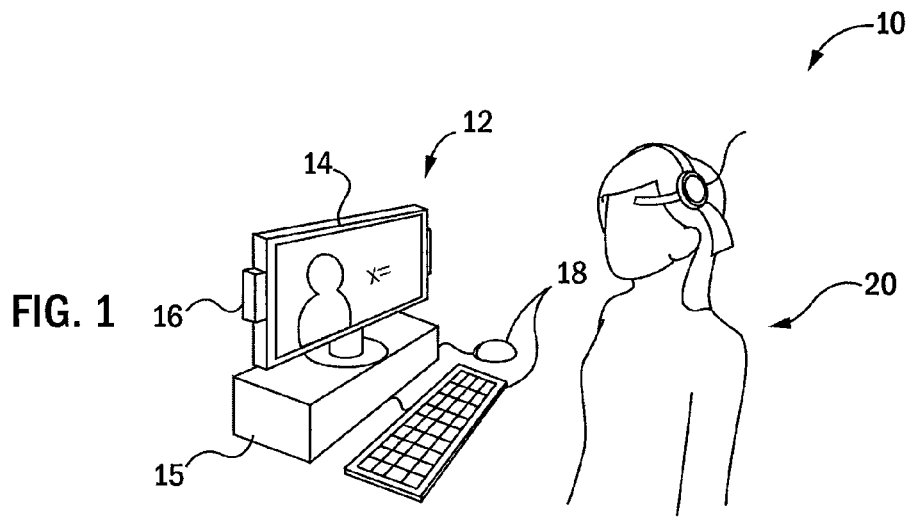
FIG. 1 is a simplified perspective view of a computer-based education system suitable for use in the present invention providing a student with a brain monitoring headset interacting with educational software.

Referring now to FIG. 1, a first embodiment of a computer-based educational system 10 employing the present invention may use a standard desktop computer system 12 providing, for example, a processing unit 15, such as a multimedia personal computer, communicating with a display screen 14 for displaying text and images and communicating with speakers 16 or the like for providing audio programming. The computer system 12 may further include standard user input devices 18 such as a keyboard and mouse for accepting input from a student 20 using the desktop computer system 12.

The student 20 may also be provided with a brain monitor 22, for example, an EEG monitoring system. Such brain monitors 22 are available commercially under the tradename NeuroSky Mindset or Mindwave EEG monitors from Neuro-Sky of San Jose Calif. as well as other vendors. Alternatively the brain monitor 22 may be a functional near infrared imaging monitor deducing brain activity through measurement of blood oxygenation in the prefrontal cortex.

Figure 2:
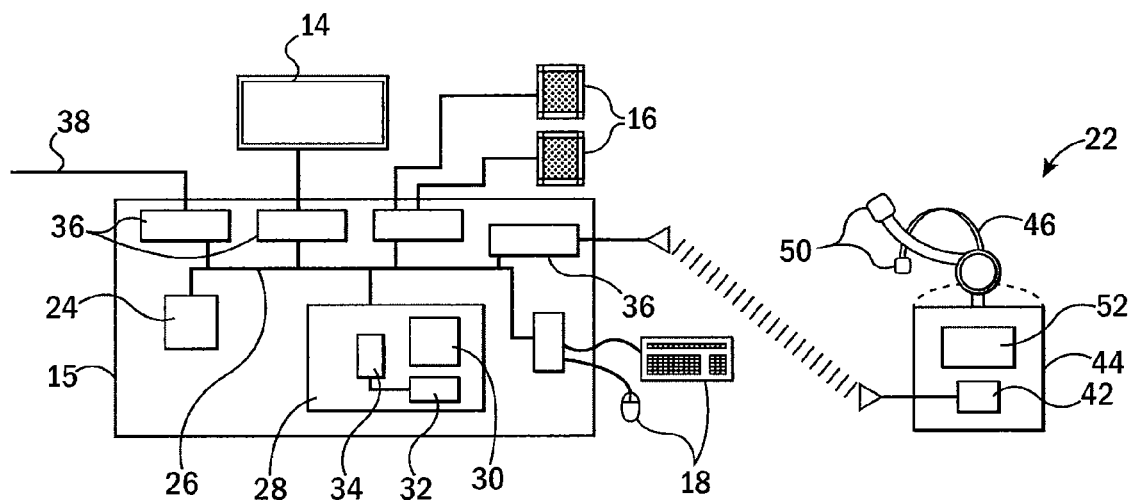
FIG. 2 is a block diagram of the computer system of FIG. 1 showing the elements of the computer system and its stored program and the brain-monitoring headset.

Referring to FIG. 2, the processing unit 15 may include one or more processors 24 communicating on a common bus 26. The bus 26 may connect the processors 24 to a variety of interfaces 36 of types well known in the art including those for connecting the processors 24 to the Internet 38, the display screen 14, the speakers 16, the brain monitor 22, and user input devices 18. The bus 26 may also connect the processors 24 with a memory 28 including, for example, random access memory and disk storage. The memory 28 may hold an operating system 30, educational program software 32 and an engagement monitoring program 34 to be described below.

The educational program software 32 in its simplest embodiment may provide for video and audio output duplicating the presentation of a human lecture albeit with the ability to interact with the engagement monitoring program 34 as will be described below. The invention is broadly applicable to a wide variety of different CBE programs including existing commercial programs with minor modification.

As noted, the brain monitor 22 may communicate with the processing unit 15 by an interface 36, for example, communicating with a Bluetooth transceiver 42 in a circuitry unit 44 of the brain monitor 22. The transceiver 42 may communicate with an internal processing unit 52 connected to a headset 46. Headset 46 generally positions sensitive electrodes 50 in contact with the skin of the patient's scalp for the receipt of EEG signals which may be processed by an internal processing unit 52 for separation of the raw EEG signal into alpha, beta, and theta waves using high speed frequency domain processing (such as the fast Fourier transform) generally understood in the art. The amplitude of the alpha, beta, and theta waves is transmitted to the interface 36 to the processing unit 15 for use by the program 34.

Figure 3:
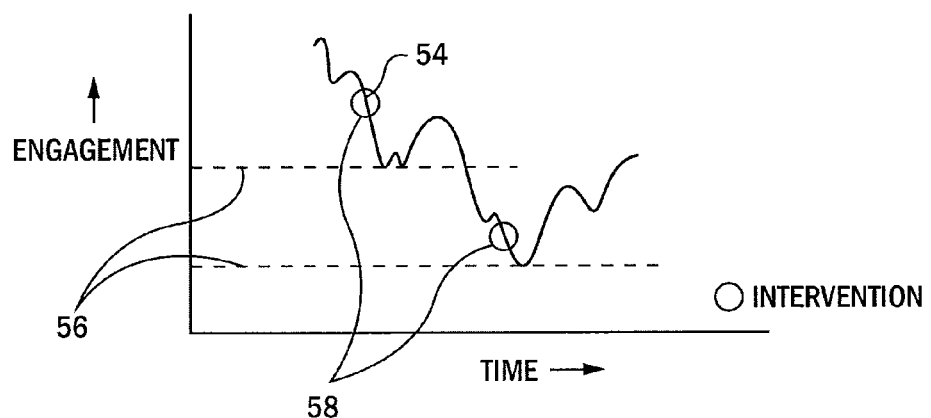
FIG. 3 is a simplified plot of an engagement signal versus time showing points of attention promoting intervention (API) according to a dynamic threshold implemented by the present invention.

Referring now to FIGS. 2 and 3, generally the educational program software 32 will present an educational program to the student 20 and the enhancement program 34 will monitor the student's brain waves to deduce an engagement level 54 during the time of the presentation. The engagement level will be compared against a dynamically determined threshold level 56 to identify effective timing of attention-promoting intervention (API) points 58 at various times during the presentation. At the times of these API points 58, the enhancement program 34 will communicate with the educational program software 32 to modify the output of the educational program software 32 to provoke increased engagement by the student 20.

Figure 4:
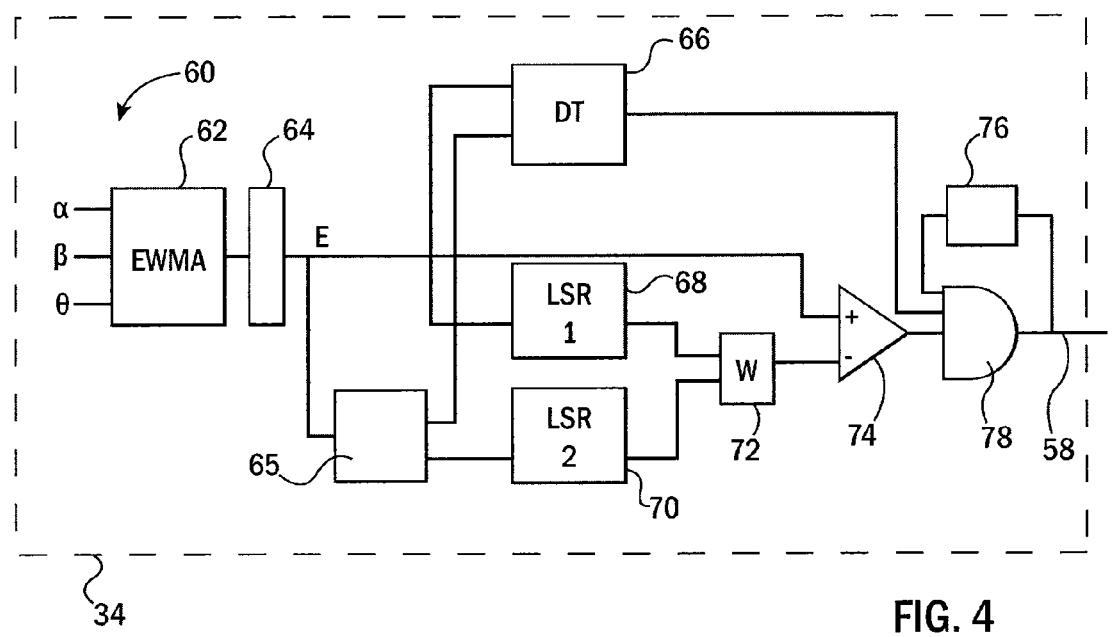
FIG. 4 is a block diagram showing determination of the timing of API based on the monitoring of brain waves from the headset of FIGS. 1 and 2.

Referring now to FIG. 4, to this end, the enhancement program 34 may receive magnitude readings of the student's alpha waves, beta waves and theta waves from the brain monitor 22 as indicated by channels 60. As is generally understood in the art, theta waves are EEG signals generally from 4 to 7 Hz, alpha waves are EEG signals generally from 8 to 12 Hz and beta waves are EEG signals generally from 13 to 30 Hz.

Each of these time varying scalar values are then processed by an exponentially weighted moving average filter 62 giving greatest weighting to most recent values according to the formula:

$$S(t) = \begin{cases} Y(t): & t = 1 \\ a*Y(t-1) + (1-a)*S(t-1): & t > 1. \end{cases} \quad (1)$$

where S(t) is the smoothed value, Y(t) is the raw EEG signal as a function of sample time t, and "a" is a regularization constant controlling the de-weighting of past values in favor of more recent values. In the experiment described below a value equal to 0.015 was used.

The EEG values are then combined to produce an engagement value E(t) per process block 64 as follows:

$$E = \frac{\beta}{(\alpha + \theta)} \quad (2)$$

where the letters in the fraction represent the alpha, beta, and theta waveforms from the brain monitor 22.

The engagement signal is then processed on a regular processing interval (e.g. 15 seconds) to evaluate a derivative threshold DT indicated by process block 66 to produce a binary value of zero or one according to the formula:

$$DT(E) = \begin{cases} 1: & \frac{\overline{dE(x)}}{dt} < \frac{\overline{dE(y)}}{dt}, \frac{\overline{dE(x)}}{dt} < 0 \\ 0: & \text{otherwise} \end{cases} \quad (3)$$

where $$\frac{\overline{dE(y)}}{dt}$$

represents the average slope of the engagement signal E(t) seen so far (as stored by buffer 65) and $$\frac{\overline{dE(x)}}{dt}$$

is the average slope of the current interval in the engagement signal.

The engagement signal E(t) is also processed on the given processing interval to evaluate two least square regression values indicated by process block 68 and 70 which minimizes the function F as follows:

$$F = \sum_{i=1}^{n} (y_i - (ax_i + b))^2 \quad (4)$$

$$\frac{\partial F}{\partial a} = 0 \text{ and } \frac{\partial F}{\partial b} = 0 \quad (5)$$

In this case, y and x represent the ordinate and abscissa of the function F in distinction from the previous example where y indicates storable data. F provides a straight line fit to E having a slope "a" and intercept "b".

A first least square regression value as defined above is calculated per process block 68 based on the processing interval of engagement data whereas the second least square regression value per process block 70 is based on all of engagement data available so far during the educational program (or more generally a longer time window than the processing interval, for example, of one half hour).

The two values of the least square regression from process blocks 68 and 70 are combined by weighting block 72 to produce a threshold value T according to the formula:

$$T = 0.05 * \overline{F(y)} + 0.95 * \overline{F(x)} \quad (6)$$

Figure 5:
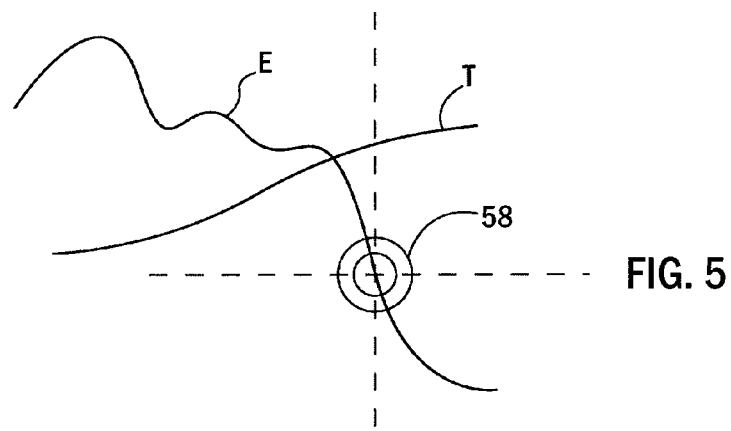
FIG. 5 is a plot similar to that of FIG. 3 showing the application of the processing of FIG. 5 to an example waveform measuring engagement.

Referring also to FIG. 5, if the current engagement value E(t) is below this threshold T, as determined by comparator 74, and the output value of process block 66 is "one" and there has not been API point 58 output in the last processing interval (as indicated by feedback timer 76), as determined by AND block 78, then API point 58 is output triggering modification of the presentation of the educational material by the educational presentation program 34 to provoke increased attention by the student 20 (shown in FIGS. 1 and 2).

Figure 6:
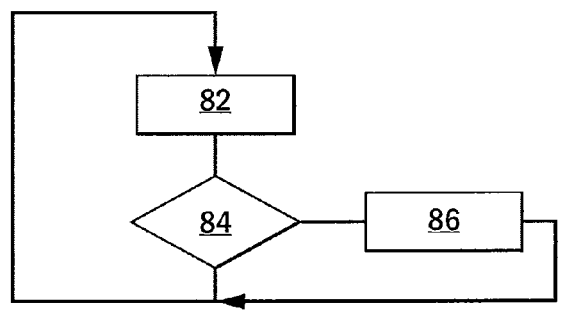
FIG. 6 is a simplified flowchart of a program executed by the computer system of FIG. 2 interacting with educational software.

Referring now to FIG. 6, as noted, the present invention operates in tandem with the presentation of an educational program by the educational program software 32, the latter presentation indicated by process block 82, where the engagement monitoring program 34 periodically checks, as indicated at decision block 84, for example on the processing interval, whether API points 58 should occur. If so the API points 58 are implemented as indicated by process block 86, as will be described below, otherwise the program returns to process block 82.

Figure 7:
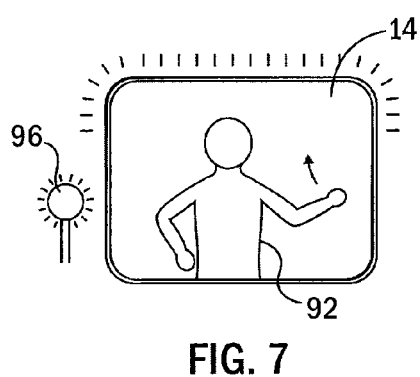
FIG. 7 is an example of API implemented on a video display providing a representation of a lecturer.
Figure 8:
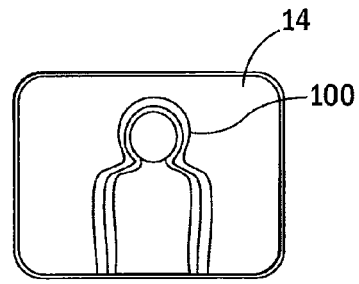
FIG. 8 is an example of alternative API for use with video displays.

Referring now to FIG. 7, one form of responding to the API points 58 may be in the generation of nonverbal immediacy cues by a computerized avatar 92 presenting a lecture on the display screen 14. These nonverbal immediacy cues may include, for example, hand gestures that will be described below. Alternatively or in addition, other modifications to the video and audio presentation through the computer system 12 may be used to implement the API points 58 including change in volume of the audio program, brightening or dimming the screen display, or providing a separate graphic indicator 96, for example, an LED or the like providing feedback with respect to the student's attention. API points 58 may also be implemented in a prerecorded video lecture, as shown in FIG. 8, by applying video effects 100 including, for example, panning, shaking, brightening or darkening, highlighting or zooming or the like to the prerecorded image. A similar effect can be obtained with changes in camera angle when multiple cameras are used to record a live lecture. The API points 58 may also be implemented by change of presentation or the introduction of a quiz or summary.

Figures 9A, 9B, 9C:
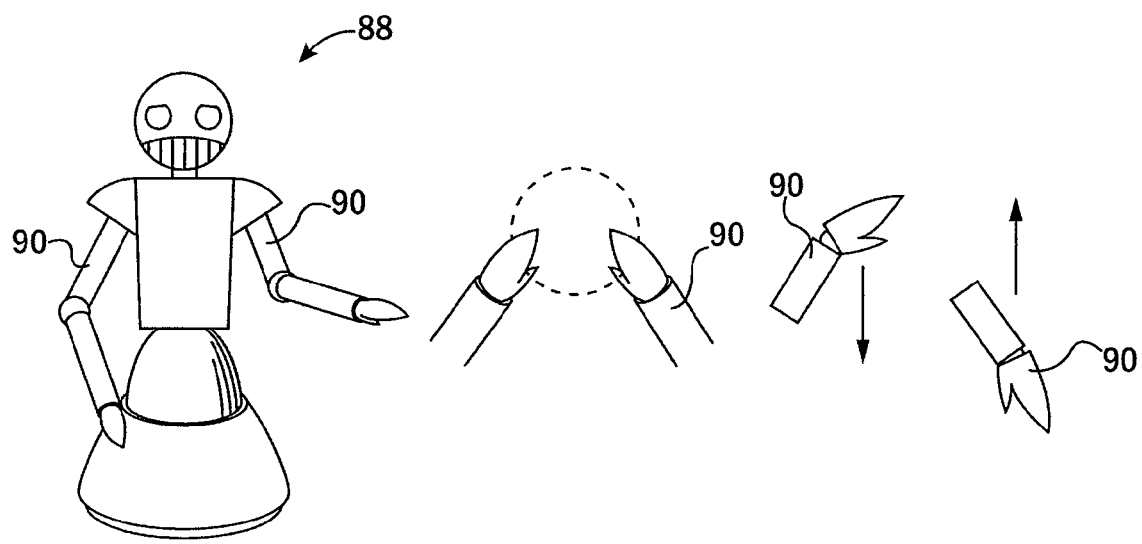
FIGS. 9a-9c are examples of API implemented by a teaching robot.

Referring now to FIG. 9a-c, in one embodiment, the educational program may be delivered through a humanoid robot 88 having articulated arms and hands 90 to make nonverbal immediacy cues in response to the API points 58. Research into gestures suggests that people use four major categories of gestures in human-human interactions: (1) iconic, (2) metaphoric, (3) deictic, and (4) beat gestures. Iconic gestures are closely related to the content of speech and represent concrete events and objects, for example, raising one's hands to indicate "higher". Metaphoric gestures allow the speaker to represent abstract concepts, such as moving one's hands in a circle to describe a cycle per FIG. 9b. Deictic gestures direct attention towards things directly around the speaker or to the parties in the interaction, such as pointing at one's self or the listener to highlight a self-experience per FIG. 9a. Beat gestures allow the speaker to emphasize certain words and phrases and may also be linked with internal processes in speech formulation, for example, rhythmic arm motion per FIG. 9c. The present invention may use any of these gestures as an immediacy cue which may be delivered without interference with verbal delivery by the humanoid robot 88 by the calling of separate arm control scripts at the times of the API points 58.

Example I

To investigate the effects of EEG-triggered adaptive immediacy cues in educational outcomes, a laboratory experiment was conducted in which participants received instruction from a humanoid robot. This experiment provided a 3×1 between-participants study in which immediacy cues displayed by a Wakamaru humanlike robot were manipulated as it told participants two narrative stories. The independent variable was the introduction of the immediacy cues and included three levels: (1) low immediacy, (2) immediacy cues at random intervals, and (3) "adaptive" cues triggered by drops in the participants' EEG-measured engagement levels determined by the dynamic thresholding process described above. The dependent variables included participants' recall of the details of the stories, self-reported learning, and EEG signals (used in post-hoc analysis to confirm that interventions successfully halted downward trends in student attention).

Experimental Procedure

In the study, each participant was presented with a memory task that assessed the participant's recall of the details of a story narrated by the robotic teacher. After signing a consent form and being given a brief description of the experiment, participants were brought into a controlled room. Here the researcher aided the participant in putting on the wireless EEG headset and ensured good connectivity. Once the headset connection was established, the researcher left the room and the participant started interacting with the robotic instructor. The human-robot interaction scenario consisted of five main phases: (1) introduction, (2) calibration, (3) learning, (4) distractor, and (5) evaluation, during which the robot spoke using a pre-recorded female voice modulated to a gender-neutral tone.

First, the robot introduced itself and asked if the participant had any prior knowledge of the story behind the twelve signs of the Chinese Zodiac.

Second, the robot then told a pre-scripted three-minute long story about the determination of animals in the Chinese Zodiac, which was used to get baseline EEG readings that were used to build the derivative and LSR thresholds. During this calibration phase, the robot maintained "eye" contact with the user by following the users head movements to make the conversation appear more natural, but did not employ other immediacy cues regardless of experimental condition. Both this and the next story used in the learning stage were chosen for their unfamiliarity to the participant population in order to ensure that participants had no prior task knowledge.

Third, in the learning phase, the robot narrated a longer ten-minute story based on the popular Japanese folk tale "My Lord Bag of Rice." During this story, robot-participant immediacy was manipulated according to experimental condition. In the adaptive condition, the robot displayed adaptive immediacy cues by increasing its volume and employing arm gestures when a drop in engagement was identified by monitoring the participants' real-time EEG engagement data. In the random immediacy cue condition, the robot raised the volume of its voice and produced arm gestures at random intervals, the number of which was determined by the number of cues made by the instructor in the last experimental trial in the adaptive condition. In the low immediacy category, the robot told the second story in the same way it told the first story, ignoring any lapses in participant attention, although still using gaze and natural head movements that were controlled autonomously to ensure consistency between participants. While displaying an immediacy cue, the robot suspended its head movement and looked toward the participant.

Fourth, after the learning phase, the robot asked the participant four questions about the Chinese Zodiac story as a distractor task which ensured that there was a break between the learning and evaluation phases for the second story.

Fifth, in the last phase, the robot presented the participant with fourteen questions about the longer story to evaluate the participants' recall ability. During this question-answer period, the time between questions was controlled by the researcher behind the scenes to account for varying answer times.

Following these questions, the experimenter re-entered the room and had the participant remove the headset and fill out a post-experiment questionnaire to obtain a subjective evaluation of participant experience. Finally, participants were debriefed by the researcher and were compensated $5 for their time.

A total of 30 participants (15 males and 15 females) took part in this experiment. Each of the three conditions had an equal number of participants (five males and five females). All participants were native English speakers and recruited from the University of Wisconsin—Madison campus. The average age was 22.3 (SD=6.88) with a range of 18-57. Prior familiarity with robots was low (M=3.23, SD=1.55) as was their familiarity with the story in the task (M=1.37, SD=1.07) in a scale of one to seven.

Objective measurements included fourteen questions that measured the participants' ability to recall the details of the "My Lord Bag of Rice" story and the participants' EEG data.

Manipulation Checks

Three different checks were made to verify the manipulations. First, examining the EEG data of participants in the low immediacy condition was used to confirm that the engagement monitoring technique successfully identified drops in attention. Second, the EEG data of participants in the random and adaptive immediacy conditions was analyzed to ensure that the robot's behaviors had a positive effect on student engagement. Finally, a five-item scale was constructed from participant responses to the post-experiment questionnaire to assess whether or not the manipulations of the robot's immediacy behavior were successful. The items asked participants how much the robot emphasized parts of story, tried to get their attention, varied the volume of its speech, used gestures, and tried to get their attention when they grew bored (Cronbach's $\alpha=0.756$).

An analysis of variance (ANOVA) was used to analyze the data from manipulation checks and objective measurements. To verify that the system was working correctly, the EEG data for participants in the low immediacy condition was processed using the above-described techniques to identify times when the instructor would have used immediacy cues had those participants been in the adaptive condition. Engagement levels were then analyzed in the 30-second timeframes before and after each possible cue using a two-way repeated measures ANOVA using participant ID as a random effect and condition, time frame, and the interaction of the two as fixed effects. This analysis found that average engagement levels 30 seconds prior to when engagement monitoring system would have directed the robot to re-engage the participant were significantly higher than the average engagement levels 30 seconds after this time, $F(1, 658.5)=7.54$, $p=0.006$, suggesting that this dynamic threshold technique was correctly identifying losses of engagement. Further EEG analysis yielded no significant differences in the 30-second windows before and after the robot employed behavioral strategies to regain attention in the random, $F(1, 658.5)=0.116$, $p=0.734$, and adaptive, $F(1, 658.5)=2.41$ $p=0.121$, conditions, showing that robot immediacy cues successfully halted downward engagement levels.

Objective Results

The analysis confirmed that participants who received targeted immediacy cues triggered by a drop in EEG-monitored engagement levels had better recall of the story than other participants. The number of correct answers out of fourteen questions was on average 6.30 (SD=3.40), 7.44 (SD=1.94), and 9.00 (SD=1.76) in the low immediacy, random immediacy, and adaptive immediacy conditions, respectively. These results showed that participants with an adaptive instructor outperformed the random condition by 23% and the low immediacy baseline by 43% with a significant difference between the low and adaptive immediacy levels, $F(1, 27)=5.87$, $p=0.022$, $\eta_p^2=0.177$, regardless of gender. No significant difference was found between the low and random conditions, $F(1, 27)=0.652$, $p=0.426$, $\eta_p^2=0.024$, or between random and adaptive conditions, $F(1, 27)=2.60$, $p=0.118$, $\eta_p^2=0.088$. A pairwise comparison, which contrasted the adaptive condition with the random and low immediacy conditions, revealed significantly improved recall accuracy in students with an adaptive instructor, $F(1, 27)=5.43$, $p=0.028$, $\eta_p^2=0.164$. Much of the variance in the model came from gender as well as users' prior familiarity with robots. When these factors were controlled for, the analysis showed even a greater difference between information recall scores in the adaptive immediacy condition and the combined scores in the low and random immediacy conditions, $F(1, 21)=7.89$, $p=0.003$, $\eta_p^2=0.291$.

It will be appreciated that the term "engagement signal" generally refers to a signal that indicates the engagement or attention or alertness of the student, and the term "engagement" in isolation should not be considered limiting. Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference, which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

References to "a microprocessor" and "a processor" or "the microprocessor" and "the processor," can be understood to include one or more microprocessors that can communicate in a stand-alone and/or a distributed environment(s), and can thus be configured to communicate via wired or wireless communications with other processors, where such one or more processor can be configured to operate on one or more processor-controlled devices that can be similar or different devices. Furthermore, references to memory, unless otherwise specified, can include one or more processor-readable and accessible memory elements and/or components that can be internal to the processor-controlled device, external to the processor-controlled device, and can be accessed via a wired or wireless network.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications, are hereby incorporated herein by reference in their entireties.

We claim:

1. A computer-based education system comprising:
a brain activity monitor providing a monitoring of brain activity of a student;
at least one electronic computer executing at least one stored program to:
(a) present an educational program to the student during a presentation duration;
(b) receive a signal from the brain activity monitor indicating a brain activity of the student to provide an engagement signal indicating student attention at multiple points in time;
(c) collect the engagement signal at the multiple points in time to identify a history of engagement of the student;
(d) produce a dynamic threshold level based upon a history of engagement of the student updated regularly during the presentation duration;
(e) compare the engagement signal of the student against the dynamic threshold level to identify a point of intervention demarcating declining attention as a function of both the engagement signal of the student and the history of engagement of the student;
(f) update the dynamic threshold level and comparison by repeating steps (c) through (e); and
(g) modify the educational program to promote student attention at times of the point of intervention.

2. The computer-based education system of claim 1 wherein the brain activity monitor is selected from the group consisting of an EEG monitor and a functional near infrared imaging monitor.

3. The computer-based education system of claim 2 wherein the brain activity monitor is an EEG monitor providing a signal including alpha, beta and theta waves from the brain.

4. The computer-based education system of claim 3 wherein the engagement signal comprises a functional combination of multiple brain waves increasing with increasing beta wave strength and decreasing with increasing alpha and theta wave strength.

5. The computer-based education system of claim 4 wherein the dynamic threshold is based on a slope of decrease in the engagement signal.

6. The computer-based education system of claim 1 wherein the dynamic threshold is based on a comparison of a slope in decrease in the engagement signal for two different time windows applied to the engagement signal.

7. The computer-based education system of claim 1 wherein the educational program is presented by a representation of a human speaker and wherein the modification of the presentation modifies a gesture of the representation of the human speaker using hand movements.

8. The computer-based education system of claim 7 wherein the representation of the human speaker is selected from the group consisting of a software agent/avatar and an electromechanical robot.

9. The computer-based education system of claim 7 wherein the hand movements are selected from categories of iconic, metaphoric, deictic, and beat gestures.

10. The computer-based education system of claim 1 wherein the educational program includes an audio signal providing spoken text and the modification of the presentation modifies the audio signal.

11. The computer-based education system of claim 10 wherein the audio signal is modified by techniques including modification selected from the group consisting of changing a volume of the audio signal and augmenting the audio signal with nontext audio signals.

12. The computer-based education system of claim 1 wherein the educational program includes a video display and the modification of the presentation provides camera effects to the video display selected from the group consisting of: change in camera angle, panning and zooming.

13. The computer-based education system of claim 1 wherein modification of the presentation interrupts the presentation to require student input.

14. The computer-based education system of claim 13 wherein the student input provides a set of evaluation questions answered by the student.

15. The computer-based education system of claim 1 wherein the modification of the presentation augments the presentation with an attention indicator.

16. A method of providing computer-based education using a computer-based education system having:
a brain activity monitor providing a monitoring of brain activity of the student;
at least one electronic computer;
the method including the step of executing on the computer at least one stored program to:
(a) present an educational program to a student during a presentation duration;
(b) receive a signal from the brain activity monitor indicating a brain activity of the student to provide an engagement signal indicating student attention at multiple points in time;
(c) collect the engagement signal at the multiple points in time to identify a history of engagement of the student;
(d) produce a dynamic threshold based upon a history of engagement of the student updated regularly during the presentation duration;
(e) compare the engagement signal to the dynamic threshold to identify a point of intervention demarcating declining attention as a function of both the engagement signal of the student and the history of engagement of the student;
(f) update the dynamic threshold and comparison by repeating steps (c) through (e); and
(g) modify the presentation of the educational program to promote student attention at times of the point of intervention.

17. The method of claim 16 wherein the brain activity monitor monitors EEG activity and including the step of generating the engagement signal from a functional combination of multiple brain waves selected to provide a function value marginally increasing with increasing beta wave strength and marginally decreasing with increasing alpha and theta wave strength.

18. A computer-based education system comprising:
a brain activity monitor providing a monitoring of brain activity of a student;
at least one electronic computer executing at least one stored program to:
(a) present an educational program offering a presentation of content to the student during a presentation duration;
(b) receive a signal from the brain activity monitor indicating a brain activity of the student to provide an engagement signal indicating student attention at multiple points in time;
(c) collect the engagement signal at the multiple points in time to identify a history of engagement of the student;
(d) produce a dynamic threshold level based upon a history of engagement of the student updated regularly during the presentation duration;
(e) compare the engagement signal against the dynamic threshold level to identify a plurality of points demarcating periods of declining attention as a function of both the engagement signal of the student and the history of engagement of the student;
(f) update the dynamic threshold level and comparison by repeating steps (c) through (e); and
(g) change the presentation of content without altering the content to promote student attention at times of the identified points.

* * * * *